(12) United States Patent
Schwoebel et al.

(10) Patent No.: US 8,899,290 B2
(45) Date of Patent: Dec. 2, 2014

(54) METHOD FOR PRODUCING AN ANALYTICAL CONSUMABLE

(71) Applicant: Roche Diagnostics Operations, Inc., Indianapolis, IN (US)

(72) Inventors: Wolfgang Schwoebel, Mannheim (DE); Joerg Dreibholz, Altrip (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/764,999

(22) Filed: Feb. 12, 2013

(65) Prior Publication Data

US 2013/0153152 A1 Jun. 20, 2013

Related U.S. Application Data

(60) Division of application No. 13/222,205, filed on Aug. 31, 2011, now Pat. No. 8,409,382, which is a continuation of application No. PCT/EP2010/052987, filed on Mar. 9, 2010.

(30) Foreign Application Priority Data

Mar. 13, 2009 (EP) .................................... 09155088

(51) Int. Cl.
*B32B 41/00* (2006.01)
*B32B 38/00* (2006.01)
*B05C 11/00* (2006.01)
*G01N 35/00* (2006.01)

(52) U.S. Cl.
CPC ...... *B32B 38/0008* (2013.01); *G01N 35/00009* (2013.01); *G01N 35/00732* (2013.01); *G01N 35/00029* (2013.01); *B05C 11/00* (2013.01); *G01N 2035/00168* (2013.01)
USPC ............. 156/350; 156/64; 156/378; 156/379; 204/403.01; 204/403.02

(58) Field of Classification Search
CPC ............. G01N 35/00732; G01N 2035/00108; G01N 2035/00168; G01N 35/00594; G01N 35/00693; G01N 33/66; G01N 2035/00851; C12Q 1/004
USPC ............... 156/64, 350, 378, 379; 204/403.01, 204/403.02
See application file for complete search history.

(56) References Cited

U.S. PATENT DOCUMENTS

| 4,476,149 A | 10/1984 | Poppe et al. |
| 4,578,716 A | 3/1986 | van Rijckevorsel et al. |

(Continued)

FOREIGN PATENT DOCUMENTS

| CA | 2050677 | 4/2003 |
| DE | 198 49 539 | 5/2000 |

(Continued)

OTHER PUBLICATIONS

International Preliminary Report on Patentability, International Application No. PCT/EP2010/052987, 10 pages.

(Continued)

*Primary Examiner* — Philip Tucker
*Assistant Examiner* — Joshel Rivera
(74) *Attorney, Agent, or Firm* — Roche Diagnostics Operations, Inc.

(57) ABSTRACT

A method for producing an analytical consumable is proposed. The analytical consumable comprises at least one carrier and at least one analytical aid connected to the carrier. At least one optically sensitive material is applied to the carrier, said material being designed to carry out at least one optically detectable alteration in the event of action of an electromagnetic radiation. In at least one coding step, at least one function information item about the analytical consumable is introduced into the optically sensitive material by means of electromagnetic radiation. The function information item is designed to enable at least one analytical instrument to use the analytical consumable correctly.

18 Claims, 2 Drawing Sheets

(56) References Cited

U.S. PATENT DOCUMENTS

| | | | |
|---|---|---|---|
| 4,935,346 A * | 6/1990 | Phillips et al. | ............ 435/14 |
| 5,216,925 A | 6/1993 | Odernheimer | |
| 5,281,395 A | 1/1994 | Markart et al. | |
| 5,286,362 A | 2/1994 | Hoenes et al. | |
| 5,340,628 A | 8/1994 | Herzog | |
| 5,515,170 A * | 5/1996 | Matzinger et al. | ............ 356/423 |
| 5,708,247 A | 1/1998 | McAleer et al. | |
| 6,045,567 A | 4/2000 | Taylor et al. | |
| 6,168,957 B1 | 1/2001 | Matzinger et al. | |
| 6,340,588 B1 * | 1/2002 | Nova et al. | ............ 506/16 |
| 6,618,957 B2 | 9/2003 | Novak et al. | |
| 6,733,655 B1 | 5/2004 | Davies et al. | |
| 6,814,844 B2 | 11/2004 | Bhullar et al. | |
| 8,409,382 B2 | 4/2013 | Schwoebel et al. | |
| 2002/0082797 A1 | 6/2002 | Deweese et al. | |
| 2002/0168317 A1 | 11/2002 | Daighighian et al. | |
| 2003/0207441 A1 | 11/2003 | Eyster et al. | |
| 2004/0015102 A1 | 1/2004 | Cummings et al. | |
| 2004/0048359 A1 | 3/2004 | Schmeling | |
| 2005/0201897 A1 | 9/2005 | Zimmer et al. | |
| 2006/0002816 A1 | 1/2006 | Zimmer et al. | |
| 2006/0006574 A1 | 1/2006 | Lang et al. | |
| 2006/0210426 A1 | 9/2006 | Hagiwara | |
| 2006/0216817 A1 | 9/2006 | Hoenes et al. | |
| 2007/0273928 A1 | 11/2007 | Robinson et al. | |
| 2008/0029606 A1 | 2/2008 | Lewis | |
| 2008/0037273 A1 | 2/2008 | Muehlemann et al. | |
| 2009/0009087 A1 | 1/2009 | Espiau et al. | |
| 2009/0090874 A1 * | 4/2009 | Roper et al. | ............ 250/484.4 |
| 2009/0212109 A1 | 8/2009 | Harttig et al. | |
| 2010/0121369 A1 | 5/2010 | Harttig et al. | |
| 2011/0108190 A1 | 5/2011 | Dagenbach et al. | |

FOREIGN PATENT DOCUMENTS

| | | |
|---|---|---|
| EP | 0 132 790 A2 | 2/1985 |
| EP | 0 299 517 A2 | 1/1989 |
| EP | 0 371 572 | 6/1990 |
| EP | 0 678 308 A1 | 10/1995 |
| EP | 1 250 954 A2 | 10/2002 |
| EP | 1 593 434 | 11/2005 |
| EP | 1 628 137 A1 | 2/2006 |
| EP | 1 826 705 A1 | 8/2007 |
| EP | 2 040 079 | 3/2009 |
| EP | 2 055 472 | 5/2009 |
| JP | 01-105170 | 4/1989 |
| JP | 3-503569 | 8/1991 |
| JP | 03-225278 | 10/1991 |
| JP | 6-175584 | 6/1994 |
| JP | 08-285856 | 11/1996 |
| JP | 11326339 A | 11/1999 |
| JP | 2004093548 A | 3/2004 |
| JP | 2006258696 A | 9/2006 |
| JP | 2009047597 A | 3/2009 |
| WO | WO 2005/012916 A1 | 2/2005 |
| WO | WO 2005/032372 | 4/2005 |
| WO | WO 2008/138473 | 11/2008 |
| WO | WO 2008/138473 A1 | 11/2008 |

OTHER PUBLICATIONS

Omicron Laserage Laserprodukte GmbH, "Omicron presents a new high-power UV-A LED module", Press Release No. 7/2006, 4 pages (including translation).

Giessen Friedberg University of Applied Sciences, "Fiber optic UV systems", Laser 2005, Halle B2, Stand 459, 4 pages. (including translation).

Giessen Friedberg Univ of Applied Sciences, "UV-A light source with a flexible light guidance system", Alchema 2006, Halle 1.2, Stand C5-F8, 3 pages (including translation).

Notice of Reasons for Rejection, Reference No. 8116155, Mailing No. 598376, Mailing Date Sep. 10, 2013, Patent Application No. 2011-553430.

* cited by examiner

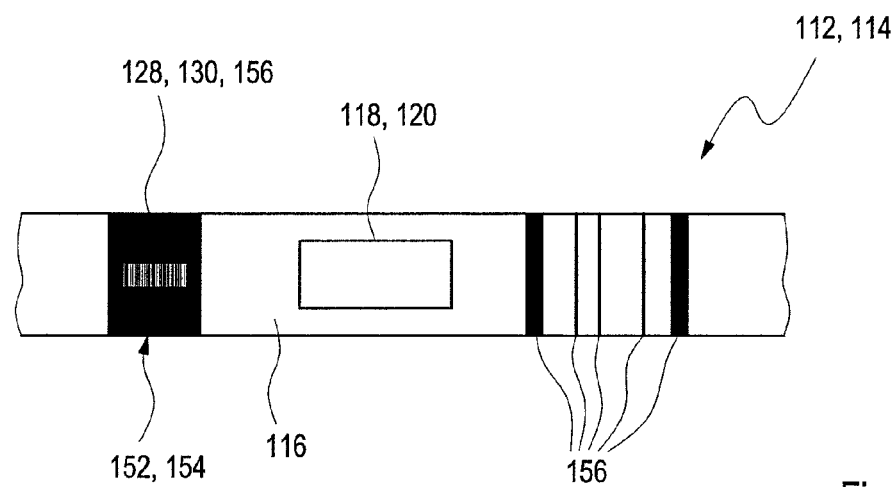
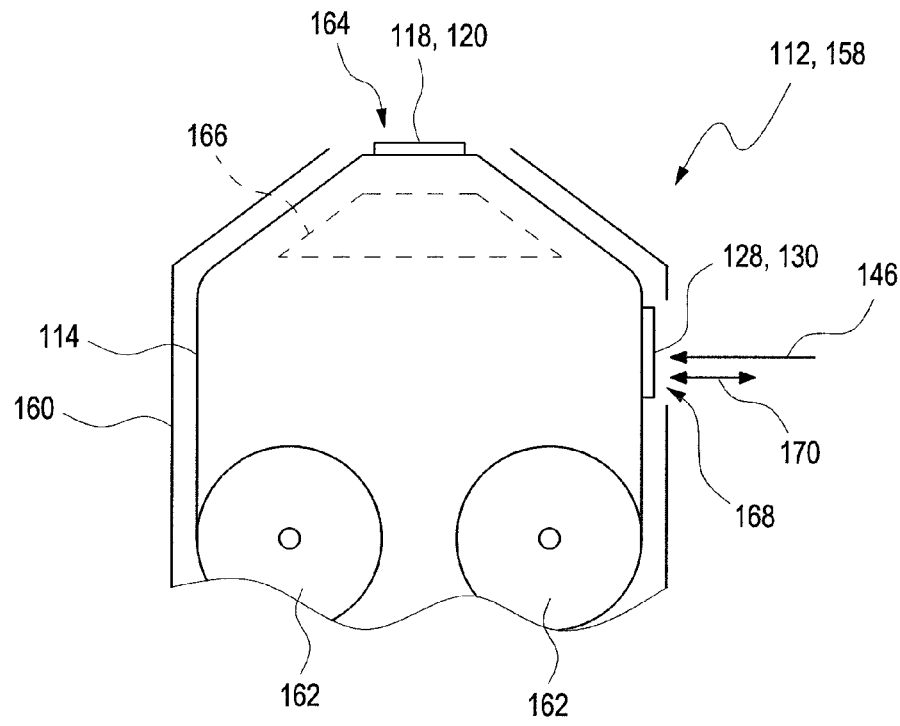

METHOD FOR PRODUCING AN ANALYTICAL CONSUMABLE

CROSS-REFERENCE TO RELATED APPLICATIONS

This application is a divisional of U.S. patent application Ser. No. 13/222,205 filed on Aug. 31, 2011, now U.S. Pat. No. 8,409,382, which is a continuation of International Application No. PCT/EP2010/052987 filed Mar. 9, 2010, which claims priority to EP Application No. 09155088.9 filed Mar. 13, 2009. Each of the referenced applications is incorporated herein by reference in its entirety.

FIELD OF THE INVENTION

The invention relates to a method and a device for producing an analytical consumable. Analytical consumables of this type are used in particular in medical diagnostics in order qualitatively and/or quantitatively to detect at least one analyte in a sample, for example a sample of a body fluid. However, other fields of application are also conceivable, for example in chemical analytics.

BACKGROUND

In medical diagnostics, in particular, numerous types of consumables are known, which are usually configured as disposable articles and have to be produced rapidly, reliably and cost-effectively. Thus, by way of example, the examination of blood samples or other samples of body fluids, for example interstitial fluid, in clinical diagnostics enables early and reliable identification of pathological states and also targeted and astute monitoring of body states.

Medical diagnostics generally presupposes that a sample of blood or interstitial fluid is obtained from the patient to be examined. For this purpose, the skin is usually perforated, for example at the finger pad or the ear lobe, with the aid of a sterile, pointed or sharp lancet in order thus to obtain a small amount of blood for analysis. Self-monitoring of blood sugar levels is a method of diabetes control that is nowadays applied worldwide. Blood sugar devices in the prior art generally have an analysis instrument which interacts with at least one analytical consumable, in particular a test element. In this case, the sample to be analysed is generally applied to a test field of the test element and reacts in the test field with one or more reagents, if appropriate, which are generally chosen in a manner specific to the analyte to be detected. This reaction can be detected, for example optically and/or electrochemically.

Analytical consumables in the form of test elements are just one exemplary embodiment of a multiplicity of consumables which are used in analytics, in particular medical analytics. Numerous further applications which use consumables are conceivable. In principle, the invention described below can be employed on all types of analytical consumables in accordance with the prior art.

When such analytical consumables are used, in particular in medical diagnostics, a number of technical challenges arise in practice, however, which have to be overcome by complex apparatus solutions. Thus, one difficulty consists in the fact that different types of analytical consumables which can be used in an analysis system can have differences among one another. Thus, by way of example, differences can arise with regard to the manufacturer and/or the production method, with regard to the detection reagents used, with regard to the analyte to be detected, with regard to the analysis method and/or analysis system to be used, with regard to the conditions under which the analysis is intended to be carried out, with regard to the parameters and/or the algorithms for the evaluation of measurements, with regard to the batch numbers, with regard to batch-specific special features, with regard to the manufacturing method, with regard to the number of analysis zones on a test element or the like. Information items about the above-mentioned differences and/or other types of differences should therefore be communicated to an analysis instrument which uses the analytical aid. In the case of analytical aids with lancets or other types of medical disposable articles, too, such article-specific information items can arise, in particular information items with regard to the manufacturer, the type of lancet, the lancet systems to be used or the like. Such items of information which are designed to enable at least one medical instrument to use the analytical consumable or components of said analytical consumable correctly are referred to hereinafter generally as function information items. Such function information items can comprise for example the abovementioned information items and/or further information items mentioned below. As an alternative or in addition, other information items can also be included. Function information items can comprise for example consumable-specific information items and/or aid-specific information items. In this case, the expression consumable-specific information items relates to information items concerning the analytical consumable as a whole, whereas aid-specific information items predominantly relate to individual analytical aids, for example individual test fields and/or lancets which are contained in the analytical consumable.

In many cases it is necessary, therefore, to correspondingly code an analytical consumable, that is to say provide it with a readable code, in order, as soon as this is necessary, to be able to provide these information items accordingly. One important exemplary application consists in automatic reading-in of functional information items, for example of consumable-specific information items, by an analysis instrument which is intended to use medical disposable articles, such as test strips, test tapes or lancets, for example. Since manual inputting and read-out of such function information items are generally unreasonable or even impracticable for the patient, various methods and systems in which function information items can be read in automatically are known from the prior art. Thus, by way of example, systems are known in which such function information items can be communicated by means of radio-frequency labels, data carriers that are to be inserted into a measuring instrument separately (for example so-called ROM keys) or similar code carriers. Such additional code carriers, as additional components, cause additional costs in production, however, which is generally undesirable. Moreover, user action is quite generally necessary, for example, insertion of the ROM key into a measuring instrument, which can integrate the possibility of incorrect operation.

Systems in which consumables themselves are coded are known from the prior art. DE 198 49 539 A1 describes a portable blood sugar measuring instrument for the self-monitoring of a diabetes patient. The measuring instrument uses a test strip for determining blood glucose, which is wound up as a tape with a plurality of measurement sections on a cassette. Said document proposes, inter alia, coding the production quality on the test tape in order to enable an automatic calibration of the blood sugar measuring instrument to the respective production batch of a tape cassette.

EP 0 299 517 A2 discloses a tape cassette for a biochemical analysis, which has a long test film with a detection reagent.

Said document proposes, inter alia, providing at the beginning of the test tape a coding region on the test tape, which comprises at least one information item. Said coding region can be read out for example by means of the detector which is used for the optical measurement.

Known coding methods, such as the coding method described in EP 0 299 517 A2, for example, have numerous disadvantages and technical challenges in practice, however. Thus, such coding methods are comparatively complex, for example, since they necessitate a structured application of marking substances. This in turn makes technically stringent requirements of production, since this structuring has to be effected with high resolution and at the same time has to be able to be adapted flexibly to the information items to be written in. Furthermore, it should be taken into consideration that the coding process has to take place under conditions of high cleanliness since analytical aids contained in the analytical consumable ought not to be contaminated by coding materials.

SUMMARY

There is provided a method and a device for producing an analytical consumable which avoid the disadvantages of known methods and nevertheless enable coding with high information density.

The method proposed can be carried out in particular using a device according to the invention, and the device can be designed to carry out a method according to the invention. In this respect, with regard to possible configurations of the device, reference may be made to the description of the method, and vice versa.

The method proposed serves for producing an analytical consumable. The analytical consumable has at least one carrier and at least one analytical aid connected to the carrier. In this case, an analytical consumable should generally be understood to mean an article which is intended for single use or for use encompassing only a few times in analytics, for example in chemical and/or biochemical and/or medical analytics. In this case, a particular main emphasis is on medical analytics and/or diagnostics, that is to say the detection of at least one analyte in a sample, in particular a liquid sample, for example a body fluid. In this case, the detection can be effected qualitatively and/or quantitatively and can comprise for example the detection of a metabolite. A particular main emphasis is on the detection of glucose in blood (blood glucose) and/or in urine and/or in interstitial fluid. However, other types of analytes can also be detected, in principle, such that for example cholesterol measurements, lactate measurements, coagulation measurements or similar measurements necessary in medical diagnostics can be carried out. A measurement in other types of liquids is also possible. In principle, the invention can also be applied to other fields of the natural sciences and/or technology in which analytics are required.

The at least one analytical aid can also be configured in accordance with the planned purpose of use. An analytical aid should accordingly be understood to mean a device which serves the respective analytical purpose of the consumable and/or supports this purpose. This device can be integrated completely with other parts of the analytical consumable, but can also be contained as a separate element in the analytical consumable. By way of example, such a purpose served by the analytical aid may reside in the provision of a sample to be analysed and/or in the analysis of the sample itself, in particular in the detection of at least one analyte. Accordingly, the analytical aid can comprise for example one or more of the following analytical aids: a test field for detecting at least one analyte in a sample, in particular for detecting a metabolite in a body fluid; a device for generating and/or providing a liquid sample, in particular a lancet. The test field can comprise for example a detection chemical having at least one detection reagent which changes at least one measurable property of physical and/or chemical nature in the presence of the at least one analyte. By way of example, the detection reagent can carry out a corresponding analyte-specific reaction which can be detected optically and/or electrochemically. With regard to the possible configurations of such test fields and/or test chemicals, reference may be made to the prior art.

The device for generating and/or providing a liquid sample can also be designed in various ways. Thus, a lancet can be provided, for example, which has a sharp-edged cutting surface and/or a tip which are designed to perforate part of a user's skin. More complex devices are also possible, however, for example devices which, besides a perforation purpose, simultaneously serve a transport purpose, that is to say for example additionally have at least one capillary and/or some other transport means. Various configurations are possible.

In the analytical consumable, one type of analytical aids can be provided, or a plurality of different types of analytical aids can also be combined. Thus, by way of example, a plurality of lancets can be provided, for example on an analytical tape, or a plurality of test fields can be provided, for example likewise on an analytical tape or test tape, or, as an alternative, an arrangement comprising, for example, alternating test fields and lancets can also be provided. Various configurations are conceivable.

The analytical consumable can be configured in various ways and comprise the at least one analytical aid, preferably a plurality of analytical aids, in various ways. Thus, by way of example, an analytical tape having a carrier tape and a plurality of analytical aids arranged on the carrier tape can be provided. In this case, a carrier tape can be understood to mean, for example, a plastic tape, a paper tape, a laminate tape, a fabric tape, a link chain or a similar, flexible and elongate carrier device. As an alternative or in addition, the analytical consumable can also comprise for example a test strip with at least one analytical aid, in particular an individual disposable, for example an individual disposable having one or more coding fields. Once again as an alternative or in addition, the analytical consumable can comprise a test disc with a plurality of analytical aids arranged on a surface and/or an edge of the test disc. Likewise as an alternative or in addition, a foldable consumable can be provided, with a plurality of analytical aids, for example according to a Leporello principle.

The carrier can also be configured in accordance with the at least one analytical consumable and the at least one analytical aid. Thus, the carrier can be configured in flexible and/or deformable fashion, for example, or can also have stiff properties, depending on the purpose of use. Thus, by way of example, the use of a deformable carrier is preferred in the case of a carrier tape and in the case of a foldable consumable, whereas rigid properties of the carrier are generally desired in the case of a test disc. The carrier can accordingly for example in turn comprise a paper material, a plastic material, a ceramic material, a fabric material or a combination of the stated and/or other materials.

Without restricting possible further configurations of the invention, the invention is described below essentially with reference to an analytical consumable in the form of a tape cassette comprising an analytical tape having a carrier tape and a plurality of analytical aids arranged on the carrier tape.

In particular once again here the main emphasis is placed on analytical aids in the form of test fields, although in general other configurations are also possible, as described above.

In production methods according to the invention, at least one optically sensitive material is applied to the carrier. The optically sensitive material is designed to carry out at least one optically detectable alteration in the event of action of an electromagnetic radiation. The optically sensitive material should preferably not be identical to the material of the carrier. The step of applying the optically sensitive material should therefore be carried out separately from the production of the carrier. As an alternative or in addition, however, other configurations are also possible, in principle, that is to say configurations in which, by way of example, the optically sensitive material is wholly or partly identical to one or a plurality of materials of the carrier. In this case, the step of applying the optically sensitive material can also be combined wholly or partly with production of the carrier itself.

The electromagnetic radiation and thus the sensitivity of the optically sensitive material can lie in particular in the visible and/or infrared and/or ultraviolet spectral range, such that there is particularly preferably a sensitivity to light. In principle, it is possible in this case to use one optically sensitive material and/or a combination of optically sensitive materials which carry out any desired optically detectable alteration. This can be for example an alteration of the color properties, an alteration of reflection properties, an alteration of absorption properties or else an alteration of a refractive index. A combination of the stated properties and/or other optically detectable properties can also be used.

In the method according to the invention, furthermore, in at least one coding step, at least one function information item about the analytical consumable is written to the optically sensitive material by means of electromagnetic radiation. The function information item is designed to enable at least one analytical instrument which interacts with the analytical consumable to use the analytical consumable correctly. The analytical instrument can comprise for example a medical instrument, for example a medical handheld instrument, in particular a handheld instrument which can be used for medical diagnostics. By way of example, this can involve a blood sugar measuring instrument having at least one measurement function and/or at least one sample obtaining function, that is to say, for example, the measurement of a blood glucose content in a blood sample and/or the generation of the blood sample. However, other configurations are also conceivable.

In this case, a function information item is generally understood to mean an information item which relates to the interaction of the analytical consumable with the analytical instrument, i.e. enables or supports this interaction. For possible contents or configurations of the function information item, reference may be made to the above description of the prior art, for example. This term is not intended to encompass information items about a defectiveness of the analytical consumable, that is to say defect information items, for example an information item about a defectiveness, a freedom from defects, a degree of quality or similar defect information items. However, such defect information items can be encompassed in addition to the at least one function information item.

In this case, hereinafter no distinction is made conceptually between the at least one function information item and the meaning contained therein and/or the physical form thereof. Thus, function information items can be present for example in a form perceptible to and decryptable by a human, for example alphanumeric characters. As an alternative or in addition, however, the function information items can also be present in coded fashion, such that their information content is perceptible and/or usable only after a corresponding decoding step. This last is also referred to as code, in which case a distinction can be made in turn for example between human-readable codes and only machine-readable codes.

Accordingly, the at least one function information item can comprise for example, as explained above, at least one consumable-specific and/or aid-specific information item. By way of example, the at least one function information item can comprise one or more of the following information items: an information item about a manufacturer and/or a production method; an information item about a detection reagent contained; an information item with regard to an analyte to be detected; an information item with regard to an analysis method and/or analysis system to be used; an information item with regard to the conditions under which an analysis is intended to be carried out; an information item with regard to parameters and/or algorithms for an evaluation of measurements, in particular at least one correction factor and/or at least one function curve; an information item with regard to batch numbers and/or at least one individual identification; an information item with regard to batch-specific special features; an information item with regard to a number of analytical aids; an information item with regard to a type of a device for generating and/or providing a liquid sample, in particular a lancet; an information item with regard to a device to be used for generating and/or providing a liquid sample, in a particular a lancet; an endurance information item, in particular an endurance date and/or an endurance restriction; a use restriction. A use restriction can restrict for example specific uses of the analytical aid in an analytical instrument if the analytical instrument reads said use restriction. By way of example, it is possible to utilize the use restriction in the analytical instrument to the effect that a specific analytical consumable or a part thereof is not permitted to be used on this instrument, or for similar purposes. By way of example, a use restriction can comprise an inhibit information item which inhibits the use on a specific instrument.

In particular, an information item about a manufacturer and/or a production method can be included. Said manufacturer and/or the production method can relate to the analytical consumable as a whole or else parts thereof, for example one or a plurality of analytical aids included in the analytical consumable. As an alternative or in addition, the function information item can comprise an information item about a detection reagent included. By way of example, a type of the detection reagent in coded form, an expiration date, a date of manufacture, a batch-specific sensitivity or the like can be included. Once again as an alternative or in addition, an information item with regard to an analyte to be detected can be included. Likewise as an alternative or in addition, an information item with regard to an analysis method and/or analysis system to be employed can be included. By way of example, it is possible to include in coded form what blood glucose measuring instrument is suitable for the respective analytical consumable and/or one or a plurality of analytical aids contained therein. In this way, it is possible for example to identify operating errors in a timely fashion, by precluding for example a situation where an unsuitable analytical instrument is used for the respective consumable, or vice versa. Furthermore, likewise once again as an alternative or in addition, an information item with regard to the conditions under which an analysis is intended to be carried out can be included. By way of example, in the case of optical test elements, parameters of an optimum illumination can be predetermined and/or, in the case of electrochemical test elements, optimum current and/or voltage parameters can be predetermined. Various other configurations are conceivable.

Once again as an alternative or in addition, an information item with regard to parameters and/or algorithms for an evaluation of measurements can be predetermined. In particular, it is possible, in this way, to predetermine for example correction factors and/or at least one function curve which may be necessary for the evaluation of an analysis. In this way, batch-specific fluctuations, in particular, can be compensated for by concomitant supply of correction factors and/or function curves for each batch of consumable and/or for each individual analytical aid in the consumable. Separate inputting of such batch-specific special features by a user and/or by a separate data carrier is not necessary. Once again as an alternative or in addition, the function information item can comprise for example a function with regard to a number of analytical aids. Thus, by way of example, it is possible to specify a total number of analytical aids in the consumable and/or a number of analytical aids that are still available and/or analytical aids that have already been used. This information can be utilized by the analytical instrument for example to request a user to procure and/or provide a new analytical consumable in a timely fashion. Once again as an alternative or in addition, an information item with regard to a type of a device for generating and/or providing a liquid sample can be included. As explained above, this device can be a lancet, in particular. The information item can be utilized for example for using a correct drive system for the respective lancet and/or precluding the use of unsuitable lancets by the analytical instrument. Once again as an alternative or in addition, an information item with regard to a device to be used for generating and/or providing a liquid sample, in particular a lancet, can also be included, such that a user can be requested for example from the outset to insert a correct device and/or a correct analytical consumable into the analytical instrument.

In contrast to the known coding methods, such as the coding method disclosed in EP 0 299 517 A2, for example, the proposed coding method of the present invention can be configured comparatively simply, yet codings with high information density can nevertheless be applied. In contrast to the known printing methods for applying colour markings, bar codes or the like, the process of applying the optically sensitive material to the carrier can be effected comparatively coarsely, in unstructured fashion or in structured fashion only with low resolution. Complex printing methods can be completely dispensed with in this case. The actual coding, which can be effected with high resolution, can subsequently be effected in a structured manner by means of the electromagnetic radiation, which can be used with high energy density.

In this case, by using suitable concentrated and/or focused beams, it is possible to obtain high resolutions, for which purpose a corresponding optical unit, for example, can be provided in the method according to the invention. In this case, it is possible to provide one or more electromagnetic radiation sources which can provide suitable electromagnetic radiation. In principle, any types of such electromagnetic radiation sources can be used. What is particularly preferred on account of the possible high energy density and the possible high degree of concentration and/or focusing, however, is the use of one or more lasers, such that the electromagnetic radiation preferably comprises at least one laser radiation. In this case, it is possible to use for example lasers in the ultraviolet spectral range and/or in the visible spectral range and/or in the infrared spectral range. Since laser radiation usually provides a very narrowband radiation, an adaptation of the electromagnetic radiation to the properties of the optically sensitive material can be effected in a targeted manner by means of a suitable choice of the wavelength of the laser radiation. Thus, by way of example, it is possible to choose an electromagnetic radiation lying in a wavelength range in which the optically sensitive material has a high absorption, for example an absorption peak. Through this targeted choice of the wavelength, it is also possible to avoid damage to further components of the analytical consumable, such as the carrier for example, by virtue of the wavelength being chosen for example in such a way that the carrier does not absorb or absorbs only slightly in the region of this wavelength, whereas the optically sensitive material absorbs to a higher degree. Thus, by way of example, the absorption, for example an absorption coefficient, of the optically sensitive material at the chosen wavelength and/or in the chosen wavelength range of the electromagnetic radiation can be made higher than the absorption of the carrier by at least a factor of two, preferably by at least a factor of ten, hundred or more.

Despite the possibility of applying the optically sensitive material to the carrier in unstructured fashion or in a structured manner only with low resolution, for example in the form of one or more coding fields having dimensions in the region of at least 500 µm, preferably of at least 1 mm, a high information density can be obtained by means of the electromagnetic radiation. Thus, in finely structured fashion one-dimensional, two-dimensional or three-dimensional structures can be introduced, for example written, into the optically sensitive material. By way of example, in the coding step, at least one one-dimensional and/or two-dimensional and/or at least one three-dimensional bar code can be introduced into the optically sensitive material. By way of example, this may involve standardized bar codes which can be evaluated by means of conventional bar code readers and/or using conventional decoding algorithms for bar codes in order to decrypt the function information item contained therein. In this case, however, a bar code can, in principle, be understood to mean any desired marking which can serve as an information carrier, in particular as an optical information carrier, for example as an information carrier having a plurality of information fields.

In general, any desired detectors can be used for reading out the at least one function information item, which detectors can be contained wholly or in part in the analytical instrument. In this case, it is possible to use additional detectors which are independent of the other functionality of the analytical instrument. As an alternative or in addition, however, it is also possible to use detectors which can be present anyway in the analytical instrument, by virtue of the fact that these detectors can be used in a multiple function. By way of example, if an analytical instrument in the form of an optical measuring instrument, for example a blood glucose measuring instrument on an optical basis, is used, then generally at least one optical detector is present in this analytical instrument, and registers for example colours or colour changes in one or more test fields of the analytical consumable. This detector can be used in a multiple function in order additionally also to read out the at least one function information item. Thus, for reading the function information item, which can be present in coded form, it is possible to use for example an instrument-side position sensor, a measurement optical unit or an additional sensor. The at least one function information item can be provided for example in one or more coding fields. These coding fields can be accessible for example on a tape through a position sensor window present in a housing of a tape cassette, through an additional window and/or through a transparent housing, for example a plastic housing.

The analytical consumable can accordingly have at least one housing in which the analytical aid is at least partly received. In this case, the housing can have at least one transparent region, in particular a window, wherein the transparent region can be at least partly transparent to the electromagnetic radiation, for example the laser radiation. As an alternative or in addition, this at least one transparent region can also be at least partly transparent to an optical detection of the optically detectable alteration, that is to say for example to an at least one detection wavelength and/or a detection wavelength range used during this detection. In this way, by way of example, a printed coding field on a tape can be written and/or read through a position sensor window, through an additional window or through a plastic housing that is transmissive to the laser or a detection wavelength.

If sensors in the analytical instrument are used in a multiple function, then it is possible to use for example a tape sensor and/or a measurement optical unit which have the capability of also reading the at least one function information item, for example a bar code with a batch calibration information item, through the window for the detection of a tape position or through a measurement window for the evaluation of a test field or a test chemical.

As explained above, the optically sensitive material can be applied to the carrier for example in the form of at least one coding field. In this case, by way of example, it is possible to use polygonal, in particular rectangular, and/or round, for example circular and/or oval, coding fields. In this case, what is advantageous about the method proposed is that said coding fields, as explained above, can be applied with low resolution. Thus, by way of example, the coding fields can have lateral dimensions, for example diameters and/or edge lengths, which are at least 200 µm, in particular at least 500 µm and preferably at least 1 mm. The actual function information item, which can be introduced with high resolution, is then introduced by means of the electromagnetic radiation, which, as described above, can be effected with high resolution without high technical outlay. In this respect, a high information density can be obtained.

The coding field can be applied using printing methods, for example, in which the optically sensitive material and/or a precursor of the optically sensitive material are printed onto the carrier. In this case, a precursor should be understood to mean materials which form the optically sensitive material after at least one conversion step. Said conversion step can be any desired physical and/or chemical step, for example a reaction and/or a phase transformation and/or drying and/or crosslinking. As an alternative or in addition it is possible to use laminating methods in which at least one film of the optically sensitive material is laminated and/or adhesively bonded onto the carrier. In this way, the coding fields can be prefabricated, for example, in order then to be applied as a whole to the carrier. By way of example, conventional labelling methods can be used for this purpose.

The at least one coding field is preferably arranged in a manner spatially separated from the at least one analytical aid. If a plurality of analytical aids are provided, then one or a plurality of specific coding fields can be assigned respectively to an individual analytical aid, a group of analytical aids or all of the analytical aids. By way of example, a tape can be provided on which a plurality of analytical aids are arranged. In this case, by way of example, in an alternating fashion before and/or after each analytical aid, every second analytical aid or every n-th analytical aid, at least one coding field can be arranged in alternating fashion with respect to the analytical aids, which carries specifically the function information item for the at least one analytical aid. However, other configurations are also possible.

The at least one coding field can also perform further functions. Thus, said at least one coding field can for example furthermore perform the function of a position marking and/or be combined with one or more position markers on the analytical consumable. By way of example, coding fields can be arranged at a plurality of predetermined and/or known positions on the analytical consumable, wherein the coding fields are designed to be used wholly or in part as position markings. This design can be effected for example by arranging them at known positions. As an alternative or in addition, the coding fields can also have a geometrical form which can be identified by the analytical instrument in a simple manner in order to carry out a position marking or a position determination in this way. Such a position marking is advantageous particularly in the case of tape cassettes. As explained above, the optically sensitive material can be configured in various ways. Thus, by way of example, said optically sensitive material can be printed as an additional colour field as a code carrier for the function information item onto the carrier, for example a reagent carrier tape. The optically sensitive material can be embodied as laser-activatable material, for example. The at least one coding field can correspondingly be embodied as a laser-activatable field, for example.

As described above, in the coding step, an optically detectable change in the at least one optically sensitive material is carried out locally. Accordingly, the at least one optically sensitive material can comprise a multiplicity of known materials which undergo such optically detectable alterations in the event of action of at least one electromagnetic radiation. By way of example, said materials can be dyes, for example dyes which, in the event of action of the electromagnetic radiation, bleach out and/or carry out a colour transition, in particular also a transition from black to white, or vice versa, which are excited to fluorescence and/or phosphorescence or which also alter their absorption and/or transmission properties in a similar manner. In this case, the dye can be used as an individual layer, but can in particular also be dissolved and/or dispersed or embedded in some other way in a matrix material. By way of example, laser-activatable dyes can be used. Furthermore, pigments can also be used, that is to say inorganic or organic, colourful or achromatic colourants which are not present in dissolved form. By way of example, laser-activatable pigments can be involved in this case. Likewise as an alternative or in addition, as explained above, the optically detectable alteration can also comprise for example an alteration of a refractive index. In this case, it is possible to use for example techniques which are typically used in holographic data storage, such that, by way of example, a hologram of this type can be introduced into the optically sensitive material. By way of example, plastic materials can be used for this purpose. In particular, it is possible here to use plastics which alter a refractive index in the event of action of the electromagnetic radiation. Thus, as an alternative or in addition to, for example, a laser-activatable print which enables a black-white transition, a suitable film material can also be structured in an optically identifiable manner, for example similarly to known holograms that can be burned into an adhesive film. By means of suitable sensors, for example likewise laser sensors, similarly to holographic data storage, the optically detectable alteration thus obtained can be identified and the at least one function information item can thus be read out again. Various configurations are conceivable.

Particularly preferably, the coding step is effected as the concluding method step or the method step that approximately concludes the production method. It is particularly preferred if the method furthermore comprises at least one calibration step, wherein at least one property of at least one analytical aid included in the analytical consumable is measured in the calibration step. Said at least one property can then be used wholly or in part as a constituent part of the at least one function information item. By way of example, calibration measurements can be carried out on one or more test fields in order to determine production-specific and/or batch-specific differences. In this way, it is possible to determine metrologically, for example, information items about the parameters and/or algorithms for an evaluation of measurements, for example correction factors and/or function curves. Other types of properties can be determined, alternatively or additionally, in the calibration step. Known detection methods can be used for carrying out the calibration step. Subsequently, this property that has been determined is preferably converted at least in part into the function information item or into a part of said function information item, and the coding step described above is subsequently carried out. In this way, the individual properties of the consumables and/or of individual or a plurality of analytical aids contained in the consumables can be determined in a targeted manner, such that for example analytical measurements which are carried out with such consumables can be carried out with high precision and with consumable-dictated fluctuations being virtually completely precluded.

By way of example, firstly during production an additional coding field, for example a colour field, can be printed as a code carrier onto a tape, for example a reference carrier tape, which is embodied as a laser-activatable field, for example. After the consumable has otherwise been at least substantially completed, in the calibration step the at least one property can be determined in order then to convert it into the at least one function information item and to apply it to the coding field. Thus, after a batch calibration by means of a laser process, for example, a bar code can be produced in a coding field, for example a pigmented field, which bar code can comprise a required batch code, for example.

A significant advantage of the downstream coding, in contrast to a coding in which a calibration information item is already printed directly onto the tape, therefore resides in the fact that the coding can be effected at a late, in particular latest possible point in time. The calibration step can be carried out in a state in which it is necessary to act on the analytical consumable only to an insignificant extent, such that an alteration of the properties of the analytical consumable and/or of individual analytical aids in the consumable can be at least substantially avoided. By means of the calibration step and the subsequent coding in the coding step, the analytical consumable itself is thus influenced only to an insignificant extent in terms of its properties. This aspect of the invention is accordingly particularly advantageous in connection with the above-described configuration of the invention in which the analytical consumable has a housing having at least one transparent region through which, by way of example the coding can be effected by means of the electromagnetic radiation. The transparency can for example also be configured at least specifically in the range of the wavelength employed for the coding and/or for the optical detection of the optically detectable alteration. In other wavelength ranges there can be lower transparency or non-transparency, for example. In contrast to this, in the case of known coding methods by means of a printing process, a complete opening of the housing would be necessary, which, however, could in turn lead to a contamination of individual or a plurality of analytical aids.

As explained above, the invention relates in a further aspect to a device for producing an analytical consumable, which device can be designed in particular to carry out a method in accordance with one or more of the embodiments described above. In this case, an analytical consumable in accordance with the description above is produced which comprises at least one carrier and at least one analytical aid connected to the carrier. The device comprises at least one application device for applying an optically sensitive material to the carrier, wherein the optically sensitive material is designed to carry out at least one optically detectable alteration in the event of action of an electromagnetic radiation. The device furthermore comprises at least one coding device which is designed to introduce at least one function information item about the analytical consumable into the optically sensitive material by means of electromagnetic radiation. As explained above, the function information item is designed to enable at least one analytical instrument to use the analytical consumable correctly.

For the possible configurations of the individual components of the device, reference may be made for example to the description above. The coding device can comprise for example at least one data processing device which, in terms of program technology, can be designed to provide the at least one function information item. In this case, the coding device can comprise a data input, for example, via which the at least one required information item, for example about a property of at least one analytical aid, can be received. The at least one information item is then converted to the function information item or a function information item which comprises this information is generated. For this purpose, by way of example, the data processing device can be designed correspondingly in terms of program technology. Furthermore, the coding device, as described above, can comprise the at least one radiation source for generating the electromagnetic radiation, for example at least one laser.

For carrying out the further method steps described above, the device can provide corresponding individual devices which are designed for carrying out the steps mentioned.

BRIEF DESCRIPTION OF THE FIGURES

Further details and features of the invention will become apparent from the following description of preferred exemplary embodiments, in particular in conjunction with the dependent claims. In this case, the respective features can be realized by themselves or as a plurality in combination with one another. The invention is not restricted to the exemplary embodiments. The exemplary embodiments are illustrated schematically in the figures. In this case, identical reference numerals in the individual figures designate identical or functionally identical elements or elements which correspond to one another with regard to their functions.

FIG. 2 shows an exemplary embodiment of an analysis tape as part of an analytical consumable.

FIG. 3 shows an exemplary embodiment of a coding step with a laser marking through a housing.

DETAILED DESCRIPTION

Figure 1:
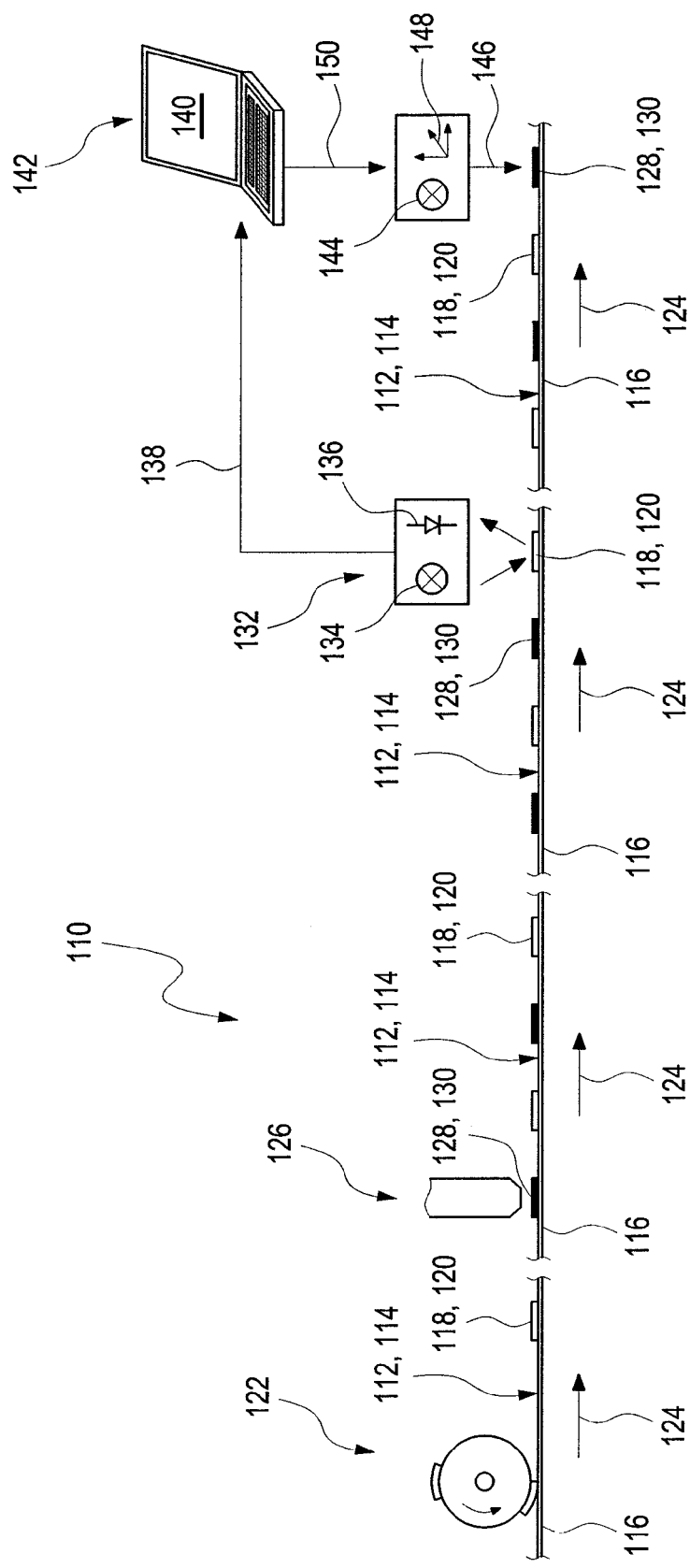
FIG. 1 shows a schematic exemplary embodiment of a device for producing an analytical consumable.

FIG. 1 illustrates an exemplary embodiment of a device 110 according to the invention for producing an analytical consumable 112. One possible exemplary embodiment of a method according to the invention for producing the analytical consumable 112 will also be explained on the basis of this device 110. It is pointed out that the device 110 can also comprise additional components not illustrated in FIG. 1, in a manner corresponding to additional possible method steps. Moreover, the order of the method steps which is indicated in FIG. 1 is not necessarily required, such that method steps also can be interchanged in their order, can be carried out laterally in parallel or can be carried out repeatedly. In this case, FIG. 1 describes an inline process, in which the method steps are carried out successively. As an alternative or in addition, however, one or more of the method steps could also be carried out temporally in parallel, for example on sub-devices which operate independently of one another.

In FIG. 1, the analytical consumable 112 is illustrated symbolically in the form of an analysis tape 114, which, in the state illustrated, is in each case still configured as a semi-finished product or intermediate product. In this description, no distinction is made conceptually between said semi finished product and/or intermediate product and the finished analytical consumable 112. The analytical consumable 112 can also be configured in some other way and can comprise, in addition to the analysis tape 114, for example also further components, as is explained in greater detail below. One example of a possible configuration of an analysis tape 114 is illustrated in FIG. 2 and is explained in greater detail below.

The analysis tape 114 comprises a carrier 116, which is configured in tape form in this exemplary embodiment. Said carrier 116, which can be configured as a carrier tape, can comprise a plastic carrier tape, for example. In the exemplary embodiment illustrated, the consumable 112 furthermore comprises a plurality of analytical aids 118, which can be configured in this case as test fields 120, for example. Each of said test fields 120 can comprise at least one detection chemical, with at least one detection reagent, which preferably reacts specifically with an analyte to be detected and carries out a colour reaction for example in the presence of the analyte. It is pointed out that the configuration of the analytical aid 118 as a test field 120 merely represents one of many possibilities. As an alternative or in addition, the analytical aid 118 can for example also comprise electrochemical test fields 120 and/or lancets and/or other types of analytical aids. By way of example, a plurality of lancets can be provided on the carrier 116. An alternating arrangement of a plurality of different types of analytical aids 118 is also possible, for example an alternating arrangement of lancets and test fields 120.

In accordance with the analytical aid 118, the device 110 comprises at least one device 122 for applying the analytical aid 118. In the exemplary embodiment illustrated in FIG. 1, said device 122 is illustrated symbolically as a labelling device, by means of which the test fields 120 can be applied in the form of labels to the carrier 116 in tape form. In this case, a running direction of the tape during production is designated symbolically by the reference numeral 124 in FIG. 1. It is pointed out that this represents one exemplary embodiment of mass production in a roll-to-roll method. As an alternative or in addition, however, it is also possible to use other types of production methods, for example batch methods, which do not use a continuous carrier 116, but even a carrier having smaller, finite dimensions.

Furthermore, the device 110 comprises an application device 126. Said application device 126 is designed to apply at least one optically sensitive material 128 to the carrier 116. In the exemplary embodiment illustrated in FIG. 1, this is done by the optically sensitive material 128 being applied in the form of coding fields 130 to the carrier 116. The application device 126 can accordingly comprise a printing device, for example, which prints the coding fields 130 onto the carrier 116 in tape form. All conventional printing methods can be used in this case, for example pad printing, screen printing, flexographic printing, inkjet printing, dispensing methods or the like. As an alternative or in addition, other application techniques can also be used, for example once again laminating techniques, analogously to the device 122, for example.

Furthermore, the device 110 in the exemplary embodiment illustrated in FIG. 1 comprises a calibration device 132. This calibration device 132, which is illustrated symbolically in FIG. 1 with a calibration light source 134 and a calibration detector 136, is designed to determine at least one property of the analytical consumable 112. By way of example, this can be a property of at least one analytical aid 118, for example of one or a plurality of the test fields 120. In this way, by way of example, calibration information items can be generated, for example correction factors and/or function curves, which are designated symbolically by the reference numeral 138 in FIG. 1. As indicated in FIG. 1, these calibration information items 138 can be provided to a data processing device 140, for example, which can be for example a constituent part of a coding device 142 explained in greater detail below. A different configuration is also possible, however. By way of example, the data processing device 140 can also be wholly or in part a constituent part of the calibration device 132 and/or a central data processing device 140 and/or a central data memory can be utilized. In the exemplary embodiment illustrated in FIG. 1, each individual analytical aid 118 is in this case calibrated by means of the calibrating device 132. As an alternative, however, these analytical aids 118 could also be calibrated in groups, or an entire calibration could be effected for the analytical consumable 112 and all analytical aids 118 contained thereon and/or all test fields 120 contained. Various configurations are conceivable and realizable for the person skilled in the art.

It is furthermore pointed out that the calibration step by means of the calibration device 132 is illustrated still on an unfinished intermediate product of the analytical consumable 112 in FIG. 1. As an alternative or in addition, however, the calibration step by means of the calibration device 132 can also be effected at a later stage, for example at a stage in which the analysis tape 114 of the analytical consumable 112 has already been combined with further components of the analytical consumable 112 to form a finished product or a higher intermediate stage of the finished analytical consumable 112. This is explained in greater detail below with reference to FIG. 3, in which the analysis tape 114 is integrated into a housing.

Furthermore, the device 110 in the exemplary embodiment illustrated in FIG. 1 comprises the coding device 142 already mentioned above. This coding device 142 can comprise, besides the optional data processing device 140 a radiation source 144 for generating electromagnetic radiation 146 and also, if appropriate, a positioning device 148. Both are merely indicated in FIG. 1. The electromagnetic radiation source 144 can comprise one or a plurality of lasers, for example. The positioning device 148 can comprise a scanning device and/or some other type of writing device, for example, such that the electromagnetic radiation 146 can be applied to individual regions of the coding fields 130 in a targeted manner. Function information items can be written to said coding fields 130 in this way. As an alternative or in addition, however, a simultaneous exposure of a plurality of regions, for example larger regions, of the coding fields 130 can also be effected, for example by the use of corresponding mask techniques. These masks can also be configured in flexible fashion, for example by the use of micromirror arrays and/or so-called SLMs (Spatial Light Modulators), such that changing information items can also be written. Various configurations are conceivable and realizable for the person skilled in the art.

In the exemplary embodiment illustrated in FIG. 1, the calibration information items 138 are converted into function information items in the data processing device 140, which, as an alternative or in addition, can also be wholly or in part a constituent part of other components of the device 110. Said function information items are designated symbolically by the reference numeral 150 in FIG. 1. As explained above, in the context of the present description, no distinction is made conceptually between the function information items and the content and/or physical form thereof. These function information items can thus be passed on for example directly to the electromagnetic radiation source 144 and/or the positioning device 148. As an alternative or in addition, however, corresponding control commands can also be communicated, for example control commands which control the radiation source 144 and/or the positioning device 148 in such a way that the function information items 150 are converted into a corresponding code in the coding fields 130 by means of corresponding local exposure.

One exemplary embodiment of such a code 152, which is designated by the reference numeral 150, can be discerned in FIG. 2. In this case, the code 152 is configured as a bar-type bar code 154 which is written to coding fields 130. By way of example, the bar code 154 can be configured in the form of a colour transition in the coding fields 130, for example by non-exposed regions having a different colour from exposed regions. As explained above, however, it is also possible to use differently configured optically detectable alterations in the coding fields 130. As an alternative to a bar-type bar code 154, it is also possible to use other types of bar codes, for example two- or three-dimensional bar codes.

The configuration of the analytical consumable 112 in accordance with FIG. 2 again comprises, as explained above, an analysis tape 114, to which analytical aids 118 in the form of test fields 120 are applied. Other configurations are also possible, as was explained above, by way of example.

In addition to these test fields 120 or analytical consumables 118, the analysis tape 114 in the exemplary embodiment shown in FIG. 2 comprises a plurality of position markings 156. These position markings, the configuration and arrangement of which are illustrated merely by way of example in FIG. 2, enable an analytical instrument, for example a blood sugar measuring instrument, to position a specific test field 120 exactly in front of a detector. The entire winding operation of the analysis tape 114 can be controlled in this way.

In the embodiment illustrated in FIG. 2, said position markings 156 are combined wholly or in part with the coding fields 130. Thus, by way of example, the optically sensitive material 128 can be used for all, some or individual ones of the position markings 156. By way of example, said optically sensitive material can be configured in such a way that, in the unexposed state, it is dark in comparison with the carrier 116, for example black. By means of a corresponding exposure with the electromagnetic radiation 146, a colour transition can then be obtained locally, for example a colour transition towards a white and/or light colour. The code 152 can therefore be configured as an "inverse" code, with light code fields on a dark background, and/or as a "normal" code with dark code fields on a light background. As an alternative or in addition, however, other configurations are also possible, for example the use of different colours.

As an alternative or in addition to the combination of the coding fields 130 with the position markings 156, however, a separate configuration of the coding fields 130 can also be effected. Thus, by way of example, in addition to the position markings 156, coding fields 130 that are spatially separated from said position markings 156, can be applied to the carrier 116.

Furthermore, it need not necessarily be the case, as indicated in the exemplary embodiment in FIG. 2, that each analytical aid 118 is assigned a dedicated coding field 130. By way of example, it is also possible for a plurality of analytical aids 118 to be combined and for this group of analytical aids 118 then to be assigned a common coding field 130. A coding is also possible in the case of which the entire analysis tape 114 is assigned only a single or a group of a few coding fields 130, which can then comprise for example function information items 150 for the entire analysis tape 114 or the entire analytical consumable 112. Various configurations are possible and realizable for the person skilled in the art in the context of the present description.

Finally, FIG. 3 schematically illustrates an analytical consumable 112 in the form of a tape cassette 158. This tape cassette 158 can comprise a housing 160, in which an analysis tape 114, for example in accordance with the configuration described in FIG. 2, can be accommodated. Said analysis tape 114 is wound through the housing 160 by means of one or a plurality of windings 162, which are merely indicated in FIG. 3.

The tape cassette 158 comprises an application position designated by the reference numeral 164 in FIG. 3. In this application position 164, it is possible for example for a liquid sample, for example a liquid sample of a body fluid (blood), to be applied to a test field 120. Furthermore, it is also possible for the measurement to be carried out in this application position 164. Thus, the tape cassette 158 can have a measurement space, for example which is designated symbolically by the reference numeral 166 in FIG. 3 and into which a corresponding detector of an analytical instrument can be introduced. However, said detector can also be fixedly integrated in the tape cassette 158. By means of said detector (not illustrated in FIG. 3), by way of example, a reflectometric measurement of an analyte-induced colour transition in the test field can be observed and subsequently, with this measurement being evaluated, a qualitative and/or quantitative conclusion about the presence of an analyte, for example a blood glucose concentration, can be drawn. However, other measurement methods are also conceivable, in principle.

The housing 160 of the tape cassette 158 furthermore comprises a window 168 in the exemplary embodiment illustrated in FIG. 3. Said window 168 can be configured for example as a simple opening in the housing 160. Preferably, in order to prevent the analysis tape 114 from being contaminated, however, said window 168 comprises a material, for example a plastic, which is transparent to electromagnetic radiation 146. In this case, there can be transparency to the electromagnetic radiation 146 used in the coding device 142 and/or transparency to a detection light 170. By means of said detection light 170, which is likewise indicated in FIG. 3, it is possible for example to read out the detectable alteration of the coding fields 130 in the region of the codes 152, for example by means of simple bar code readers. Other configurations are also possible.

The tape cassette 158 shown in FIG. 3 affords the advantage that it can firstly be substantially completed apart from the calibration step described above. Afterwards, the calibration step can be carried out, for example as described with reference to FIG. 1. In a coding step following the calibration step, the function information items 150, containing calibration information items 138, for example, can then be written to the coding fields 130 or individual ones or one of said coding fields 130 by means of the electromagnetic radiation 146, for example by means of a laser beam, through the window 168. During this coding operation, the analysis tape 114 is completely protected by the housing 160, such that no contaminants or other harmful environmental influences can affect the analysis tape 114.

Afterwards, during operation of the analytical consumable 112, for example through the window 168, the code 152 can be read out again in order to recover the function information items 150. This read-out can be effected for example by means of a detector which is present anyway in an analytical instrument. Thus, by way of example, the read-out of the function information items 150 can be effected in the application position 164 itself, for example by means of the same detector which also evaluates the test fields 120 and the discolourations thereof. As an alternative or in addition, it is also possible to use other detectors, for example detectors for detecting position markings 156. This can for example likewise again be effected in the application position 164. As an alternative or in addition, such detectors for the position markings can also be arranged such that these emit and/or register detection light 170 in the region of the window 168, in order in this way to register the position markings 156 and/or the codes 152. Various configurations are conceivable.

Although embodiments of the invention have been described using specific terms, such description is for illustrative purposes only, and it is to be understood that changes and variations obvious to the skilled artisan are to be considered within the scope of the claims that follow and their equivalents.

LIST OF REFERENCE SYMBOLS

110 Device for producing an analytical consumable
112 Consumable
114 Analysis tape
116 Carrier
118 Analytical aid
120 Test fields
122 Device for applying the analytical aid
124 Running direction
126 Application device
128 Optically sensitive material
130 Coding fields
132 Calibration device
134 Calibration light source
136 Calibration detector
138 Calibration information items
140 Data processing device
142 Coding device
144 Radiation source
146 Electromagnetic radiation
148 Positioning device
150 Function information items
152 Code
154 Bar code
156 Position markings
158 Tape cassette
160 Housing
162 Winding
164 Application position
166 Measurement space
168 Window
170 Detection light

What is claimed is:

1. A device for producing an analytical consumable that includes at least one carrier and at least one analytical aid connected to the carrier, wherein the analytical aid includes one of an analytical aid that is sensitive to an analyte and an analytical aid that comprises a device for generating or providing a liquid sample, wherein the device comprises:

at least one application device configured to apply an optically sensitive material to at least one coding field of the carrier, wherein the optically sensitive material is configured to carry out at least one optically detectable alteration by action of an electromagnetic radiation from a radiation source; and at least one coding device including a data processing device configured to convert at least one calibration information item regarding the analytical aid into a function information item about the analytical consumable, wherein the coding device is configured to receive the function information item from the data processing device and introduce by electromagnetic radiation the function information item about the analytical consumable into the optically sensitive material by an optically detectable alteration of the optically sensitive material of the coding field, wherein the function information item enables at least one analytical instrument to operate correctly with the analytical consumable.

2. The device according to claim 1, wherein the electromagnetic radiation comprises a laser radiation.

3. The device according to claim 1, wherein the coding device is configured to introduce at least one of at least one one-dimensional, at least one two-dimensional, and at least one three-dimensional bar code into the optically sensitive material.

4. The device according to claim 1, wherein the application device is configured to apply the optically sensitive material to the carrier to form the at least one coding field.

5. The device according to claim 4, wherein the application device is configured to apply the coding field in the form of a polygonal coding field.

6. The device according to claim 4, wherein the application device is configured to apply the coding field in the form of a round coding field.

7. The device according to claim 4, wherein the application device is configured to apply the coding field by printing the optically sensitive material or a precursor of the optically sensitive material onto the carrier.

8. The device according to claim 4, wherein the application device is configured to apply the coding field by laminating or adhesively bonding a film of the optically sensitive material onto the carrier.

9. The device according to claim 1, wherein the coding device is configured to alter at least a reflection property of the optically sensitive material with the electromagnetic radiation.

10. The device according to claim 1, wherein the coding device is configured to alter at least a colour property of the optically sensitive material with the electromagnetic radiation.

11. The device according to claim 1, wherein the coding device is configured to alter at least an absorption property of the optically sensitive material with the electromagnetic radiation.

12. The device according to claim 1, wherein the coding device is configured to alter at least a refractive index of the optically sensitive material with the electromagnetic radiation.

13. The device according to claim 1, wherein the optically sensitive material comprises a dye dissolved or dispersed in a matrix material.

14. The device according to claim 1, wherein the optically sensitive material comprises a pigment.

15. The device according to claim 14, wherein the pigment comprises a laser activatable pigment.

16. The device according to claim 1, wherein the function information item comprises at least one selected from the group consisting of: a manufacturer; a production method; a detection reagent contained; an analyte to be detected; an analysis method to be used; an analysis system to be used; conditions under which an analysis is carried out; parameters for an evaluation of measurements; algorithms for an evaluation of measurements; at least one correction factor for evaluation of measurements; at least one function curve for evaluation of measurements; batch numbers; at least one individual identification; batch-specific special features; a number of analytical aids; a device for generating or providing a liquid sample; a lancet for generating or providing a liquid sample; an endurance information item including at least one of an endurance date or an endurance restriction; and a use restriction.

17. The device according to claim 1, wherein the at least one coding device is configured to convert the function information item into a code that is inscribed into the optically sensitive material of the coding field by action of the electromagnetic radiation from the radiation source.

18. The device of claim 1, further comprising:

a calibration device including at least one calibration light source and a calibration detector, the calibration device being configured to determine the at least one calibration information item about the analytical aid of the analytical consumable by operation of the calibration light source and calibration detector, the calibration device further being configured to provide the calibration information item to the data processing device for conversion by the data processing device into the function information item.

* * * * *